(12) United States Patent
Hayes et al.

(10) Patent No.: US 6,334,851 B1
(45) Date of Patent: Jan. 1, 2002

(54) METHOD FOR COLLECTING INTERSTITIAL FLUID FROM THE SKIN

(75) Inventors: Donald J. Hayes, Plano; David W. Taylor, Richardson; David B. Wallace, Dallas, all of TX (US)

(73) Assignee: MicroFab Technologies, Inc., Plano, TX (US)

( * ) Notice: Subject to any disclaimer, the term of this patent is extended or adjusted under 35 U.S.C. 154(b) by 0 days.

(21) Appl. No.: 09/567,915

(22) Filed: May 10, 2000

Related U.S. Application Data

(60) Provisional application No. 60/133,360, filed on May 10, 1999.

(51) Int. Cl.$^7$ .............................. A61B 5/00; B65D 81/00
(52) U.S. Cl. .......................................... 600/573; 606/2
(58) Field of Search ................................ 600/309, 310, 600/573; 606/2, 9, 10; 604/19

(56) References Cited

U.S. PATENT DOCUMENTS

| | | | |
|---|---|---|---|
| 3,769,963 A | 11/1973 | Goldman et al. | 600/476 |
| 3,821,510 A | 6/1974 | Muncheryan | 219/121.79 |
| 3,910,276 A | 10/1975 | Polanyi et al. | 606/10 |
| 4,521,194 A | 6/1985 | Myers et al. | 433/215 |
| 4,686,979 A | 8/1987 | Gruen et al. | 606/3 |
| 4,784,135 A | 11/1988 | Blum et al. | 606/3 |
| 4,818,230 A | 4/1989 | Myers et al. | 433/215 |
| 4,826,431 A | 5/1989 | Fujimura et al. | 433/29 |
| 4,940,411 A | 7/1990 | Vassiliadis et al. | 433/215 |
| 5,092,864 A | 3/1992 | Hayes et al. | 606/10 |
| 5,123,902 A | 6/1992 | Muller et al. | 604/21 |
| 5,267,856 A | 12/1993 | Wolbrasht et al. | 433/29 |
| 5,617,851 A | * 4/1997 | Lipkovker | 600/573 |
| 6,056,738 A | * 5/2000 | Marchitto et al. | 606/2 |
| 6,077,660 A | * 6/2000 | Wong et al. | 435/4 |
| 6,173,202 B1 | * 1/2001 | Eppstein | 604/20 |
| 6,240,306 B1 | * 5/2001 | Rohrscheib et al. | 600/316 |
| 6,251,100 B1 | * 6/2001 | Flock et al. | 606/2 |

* cited by examiner

*Primary Examiner*—Eric F. Winakur
*Assistant Examiner*—Charles Marmor, II
(74) *Attorney, Agent, or Firm*—Locke Liddell & Sapp LLP

(57) ABSTRACT

A carrier film has one or more openings or wells loaded with a meltable absorbing substance for absorbing laser energy. The carrier film has a clear film which covers one side of the opening containing the absorber substance and the open side of the opening in the carrier film is positioned adjacent to the skin and irradiated through the clear cover film by a laser beam. The melted laser energy absorbing substance is ejected to form a spot laying on the skin. After moving the carrier film, a laser beam impinges the spot thereby raising a tiny blister on the skin containing interstitial fluid. The interstitial fluid is collected for diagnosis and analysis. A method of making and loading the carrier film with a digitally operated dispenser of the type used for ink jet printing is disclosed. Special construction of the opening appears to enhance ejection.

13 Claims, 6 Drawing Sheets

METHOD FOR COLLECTING INTERSTITIAL FLUID FROM THE SKIN

CROSS REFERENCE TO RELATED APPLICATIONS

This application is a continuing application from U.S. Provisional application serial no. 60/133,360, filed May 10, 1999 for which benefit is claimed under §119(e).

BACKGROUND OF THE INVENTION

1. Field of the Invention

The invention lies in the field of medical diagnostic procedures and devices.

2. Background of the Prior Art

There is a need for obtaining small samples of human interstitial fluid from the skin for the purpose of analyzing this fluid for biologically relevant molecules and electrolytes that may be found therein. More particularly, there is a need for carrying out the process of releasing and collecting the interstitial fluid for glucose measurements which is useful for diabetics. The most common current techniques for obtaining body fluid for glucose measurements is done by pricking the skin with a sharp object to create a small drop of blood. This sample can then be collected and analyzed in a test kit to determine the glucose contents. The process of pricking the skin to produce fluid samples is obviously undesirable because of the pain it creates. It would be desirable to have a more painless method of collecting and releasing interstitial fluid for this and other purposes.

SUMMARY OF THE INVENTION

This application discloses a new method for releasing interstitial fluid from skin for collection or measurement, such as for glucose determinations. The method avoids the psychological and physical pain of pricking the finger with a sharp instrument.

A carrier film having at least one opening and preferably a series of spaced openings is provided for use with a laser which produces a laser beam. The openings in the carrier film contain a meltable absorber substance selected to absorb energy from the laser beam and may include an aperture in the carrier film adjacent the opening or more than one aperture adjacent a plurality of openings. The carrier film has a base layer having the openings for the meltable absorber substance and a cover layer which covers one open side of the openings to form a well filled with absorber substance, having one open side. The carrier film is placed over the skin with the open side of the opening containing the meltable absorber substance positioned facing the skin. The laser is positioned over the carrier film with the beam it produces directed upon the absorber substance and passing through the cover film of the carrier.

Upon energizing the laser to produce the laser beam, the meltable absorber substance is melted and substantially instantaneously ejected from the opening in the carrier film and then transferred with velocity to the surface of the skin where it becomes a spot capable of absorbing laser energy. The carrier film can be moved away or indexed to the aperture whereby the laser can be employed (or a different laser) to project a laser beam onto the spot of absorber substance on the skin thereby raising a tiny blister containing interstitial fluid on the skin in the area where the spot was formed. The interstitial fluid is then available by various conventional means for collection by breaking the blister and taking the interstitial fluid for testing or analysis.

A method of making the carrier film is disclosed. A carrier film base member with spaced openings is supported on a flat support and loaded with meltable absorber substance from a digitally operated heated printhead of the type used for "jetting" materials, similar to an ink jet for a computer printer. Indexing of the carrier film strip or the printhead sequentially fills the openings with the absorber substance. A cover is preferably adhesively laminated over the openings containing the meltable absorber substance creating a well-like opening that has an open side from which the material will be ejected when activated by a suitable laser beam. Both the cover strip and adhesive are selected to allow the laser beam to be focused on the meltable absorber substance inside the openings. A cover strip may be made in a batch process or, for example, in a reel-to-reel continuous process using flexible film technology. The carrier material is preferably a laminated carrier film although it is conceivable that a blind opening could be produced in a film having the requisite clarity to passage of laser energy in the nature of a blind opening.

The well-like openings from which the meltable absorber material will be ejected may include a nozzle which is smaller than the opening itself and a gas bubble created in the back of the opening by the manner in which the opening is filled with the absorber substance. Upon melting of the absorber substance in response to impingement by a laser beam, the nozzle and gas bubble enhance the ability of the carrier strip to eject a melted droplet of the absorber substance with a certain amount of velocity onto the skin where it flattens to form a spot for subsequent steps.

It is easy to visualize a relatively small machine containing a carrier film with spaced openings and apertures which can be placed over a patient's arm for analysis. First the laser is triggered to deposit a spot of the absorber substance on the skin, then the carrier film is indexed to an opening whereby the same laser could impact the spot on the skin to form the blister which raises interstitial fluid from the skin. Collection of the interstitial fluid could be mechanized or simply taken from the tiny blister by conventional means.

DETAILED DESCRIPTION OF THE INVENTION

Figure 1:
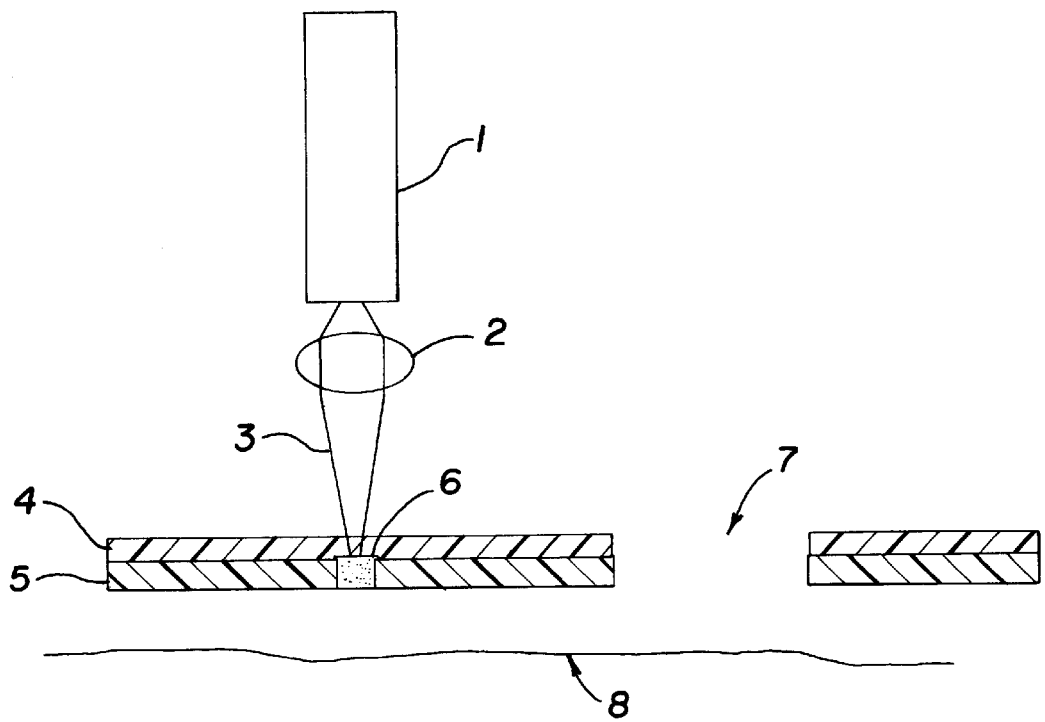
FIG. 1 is a side elevational view of the combination of a laser source focusing on a disposable laminated film strip in an area containing meltable absorber substance.

FIG. 1 schematically illustrates a set-up for depositing a laser absorbing substance from a disposable film laminate onto the surface of a person's skin. A laser source 1 is capable of supplying enough energy in a pulse or on/off format to heat a meltable or thermoplastic material selected to absorb the laser energy, which forces the absorber substance out of an opening. The laser source 1 can make a hole into the skin if proper absorption of the laser energy takes place. Laser 1 is focused through a lens 2 capable of focusing a laser energy onto the meltable absorbing substance and the skin surface if positioned properly. A laser beam 3 is focused through lens 2 onto a target 6 comprising a meltable absorber substance formulated to absorb the laser energy. The absorber substance is formulated to contain an appropriate dye or particle filler material, such as carbon black. The laser energy absorbing substance may be a thermoplastic substance, such as a polymer, a thixotropic substance that becomes fluid when heated, a greaselike or wax composition or any other carrier for the absorbing pigment or dye which melts or changes viscosity when irradiated with a suitable laser wave length. The term "meltable" should be considered as including such substances. U.S. Pat. No. 5,092,864 which discussed methods of "jetting" dyes onto tissue for the purpose of increasing laser energy absorption efficiency for tissue welding, tissue cutting, tissue ablation, hole making, etc. is incorporated herein by reference.

The meltable absorber substance is contained in a disposable laminate comprising a polymer base material 5 of such a character that uniform holes can be formed into it by means of known processes such as excimer laser ablation, hole punching, photolithography, etc. After the meltable absorber material 6 is placed in an opening in polymer base material 5, it is covered with a layer of polymer material 4 which is transparent to the laser energy. Polymer material film is selected to have good transmission to laser energy at the specific laser wave length used in laser source 1. The disposable laminate is shown positioned just above a patient's skin 8 and contains an opening 7 which comprises an aperture through the laminated film structure for purposes to be described. The skin would be positioned a few millimeters from the film surface. It is to be understood that the figures are elevational views which do not show connecting portions of the film laminate on either side of aperture 7. In a preferred embodiment, this substrate is a continuous strip which may have continuous side edge portions much like the sprocket tracks on movie film. The term film is meant to include primarily flexible material up to tat least a thickness of 0.015 inches. Prototypes have been made where the base substrate layer 5 was actually made from glass microscope slides which are only slightly flexible.

Figure 2:
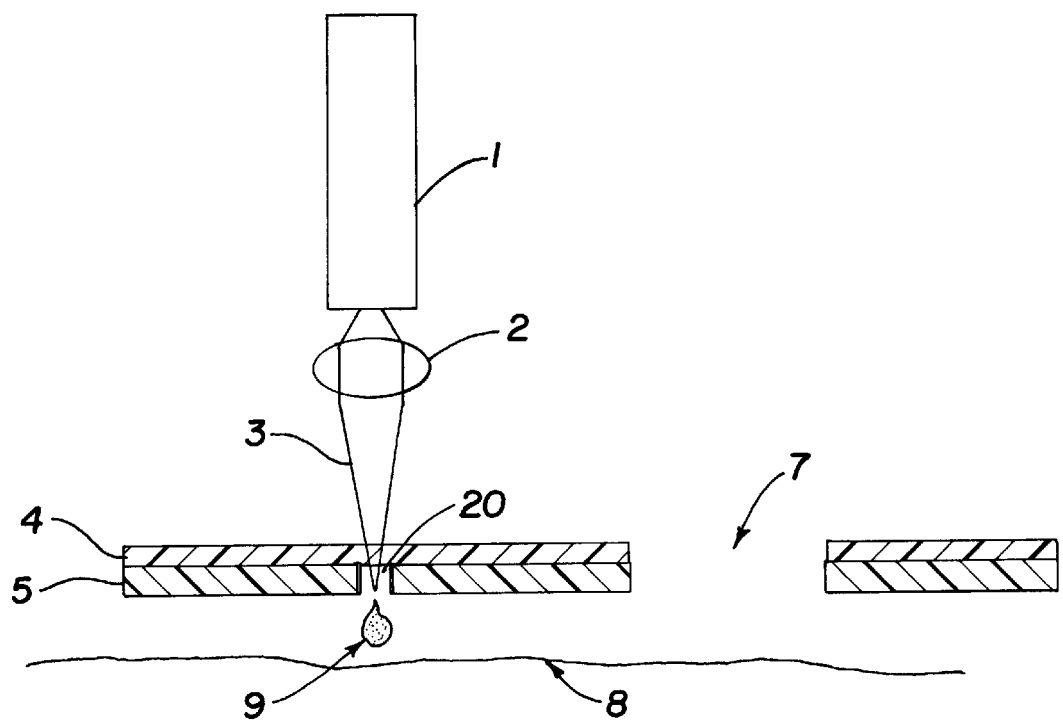
FIG. 2 shows the apparatus of FIG. 1 after the meltable absorber substance has been melted by the laser and ejected toward a patient's skin.

FIG. 2 illustrates the droplet ejection process of the apparatus found in FIG. 1. The laser 1 is placed over the carrier film 4 and 5. The beam 3 the laser produces is focused through a lens 2 onto meltable absorber substance 6 selected to absorb energy from laser beam 3. Meltable absorber substance 6 is contained in an unnumbered opening (or plurality of openings) in substrate strip 5. The opening containing substance 6 has an open side facing skin 8. Laser beam 3 is positioned to pass through the clear layer 4 before it reaches the meltable absorbing substance 6. The energy absorbed in substance 6 forces it to melt and ejects the melted substance out of the only opening available in the form of a droplet 9. In the orientation of FIG. 2, the upper side of the opening containing substance 6 is blocked by clear film 4 but open in the direction of skin 8, facing skin 8. Because of the laser energy absorbing characteristic of substance 6, it is rapidly heated with laser energy in a manner similar to the thermal ink jet effect which occurs in commercial ink jet printers from companies like Hewlett Packard, Cannon and Lexmark. This rapid heating causes the meltable absorber substance 6 to melt and rapidly expand forming droplet 9. Droplet 9 is thereby projected toward skin 8. Pressure is believed to contribute to the ejection of the melted substance due to vaporization of a portion of the substance from the heat produced by absorption of laser energy.

Figure 3:
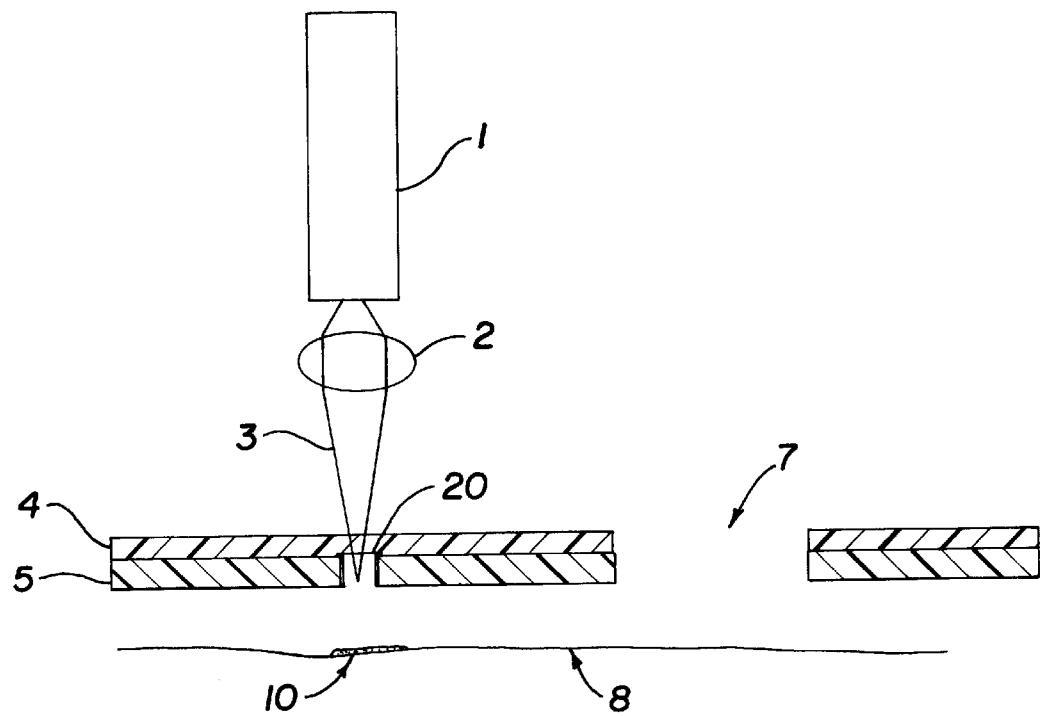
FIG. 3 shows how the melted absorber substance of FIG. 2 has impacted and spread on the surface of the patient's skin.

FIG. 3 illustrates a continuation of the process showing how droplet 9 becomes a spot 10 of meltable absorber substance on skin surface 8. The size of spot 10 on the skin and the thickness will be dependent upon the amount and wave length of the energy produced by the laser pulse, the amount of substance 6 and the liquid properties of the droplet 9 at impact. The laser can actually vaporize a small portion of the material 6 generating a pressure within the opening which contains substance 6 which drives the melted droplet 9 toward skin 8. The desired size of the spot 10 would depend upon the volume of the interstitial fluid to be collected. A range of about 100 micrometers to perhaps 2000 micrometers would appear to be in the preferred range. Even so, it should be recognized that the diameter of the spot 10 is very small. The drawings are enlarged for clarity.

Figure 4:
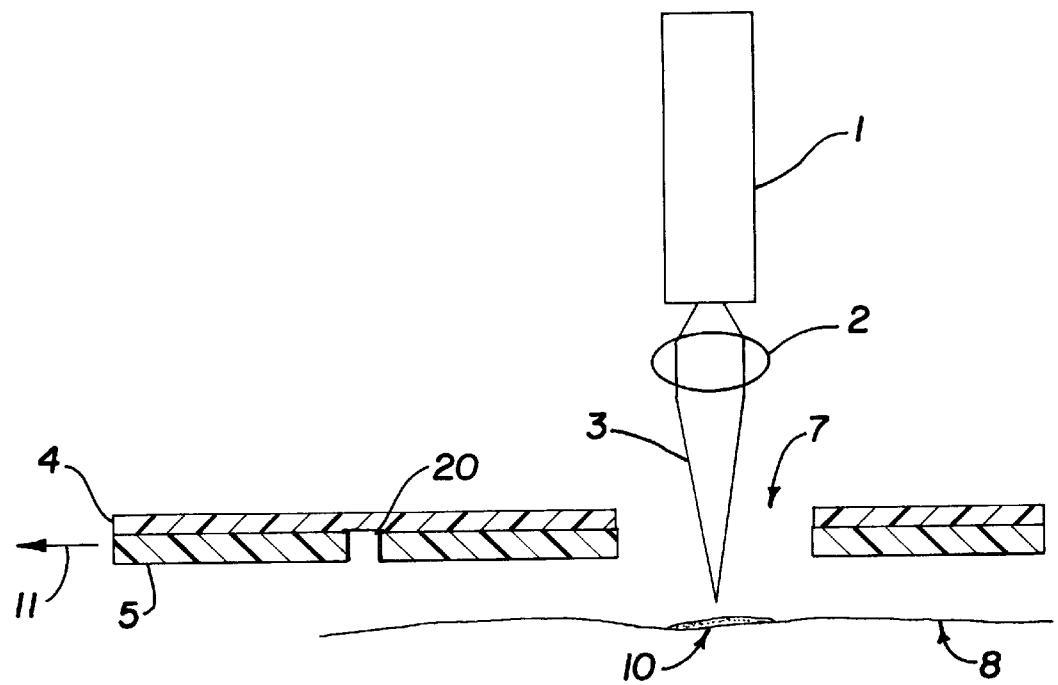
FIG. 4 shows the apparatus of FIGS. 1–3 wherein the strip of laminated polymer film material has been indexed in a horizontal direction to position the film over an aperture for the next step in the process.

The stage is now set for the spot to be used to absorb laser energy in a subsequent step to release interstitial fluid from the skin. FIG. 4 illustrates a continuation of the process shown in FIGS. 1–3. In FIG. 4, the carrier film 4 and 5 has been moved horizontally or "indexed" by an indexing means relative to skin 8 (or the skin moved relative to the film) so that aperture 7 is located between the spot of absorber substance 10 on the skin and the beam 3 produced by laser 1. Now the process is continued by operating the laser, while directing beam 3 produced by laser 1 to the spot 10 of absorber substance on skin 8, to thereby create a tiny blister containing interstitial fluid on the skin in the area where the spot 10 was formed. It is believed that indexing means for mechanically indexing carrier film 4 and 5 are circumstances which need not be described as being well known by persons of ordinary skill in the art. It might be noted that while film or sheet 4 is shown to be discontinuous at aperture 7, it is capable of passing laser energy and could cover the top of aperture 7 at some reduction in efficiency.

Figure 5:
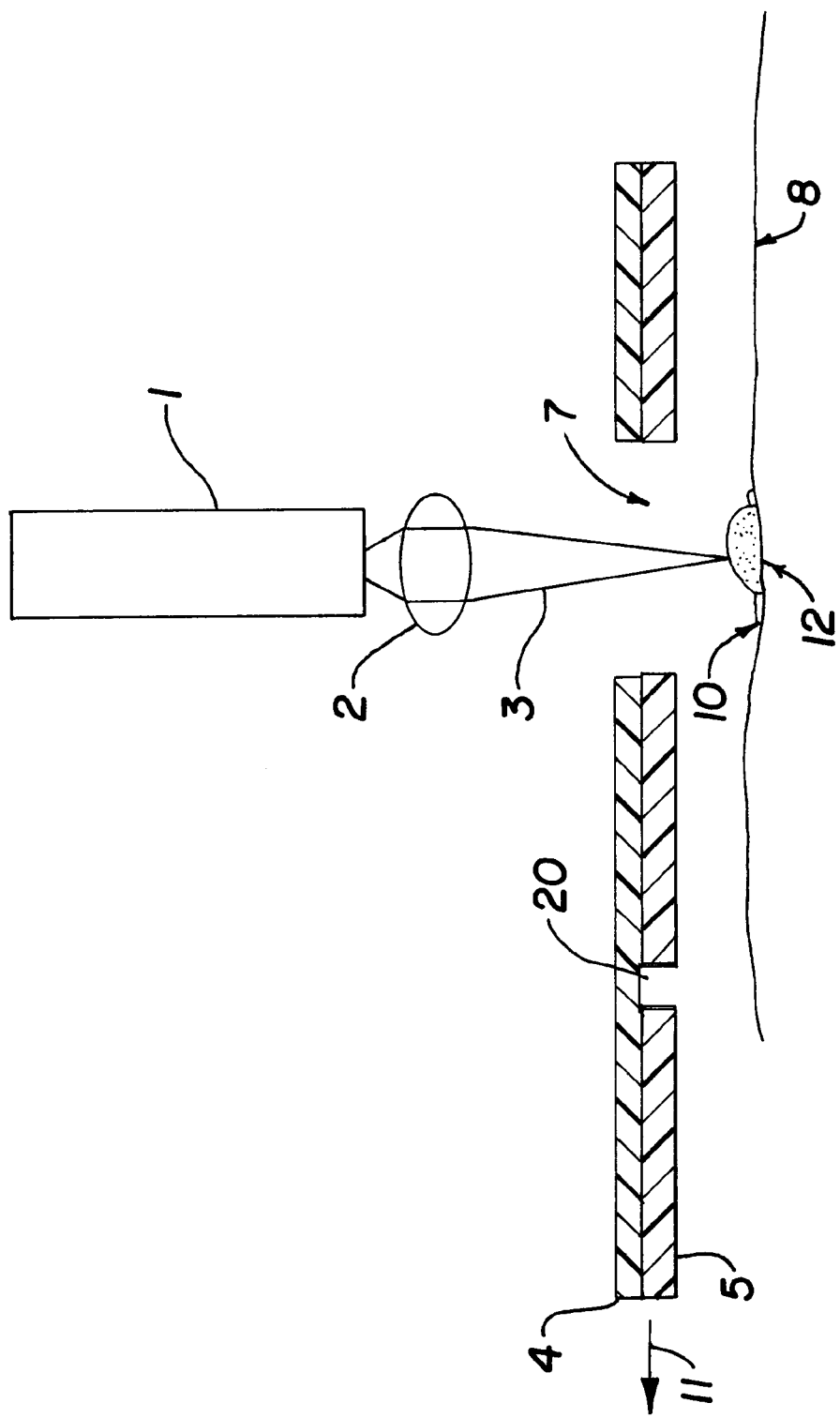
FIG. 5 illustrates the application of the focused laser beam upon the spot of FIG. 5 whereby thermal heating of the skin surface forms a tiny blister containing interstitial fluid.

FIG. 5 illustrates the result of the interaction of laser beam 3 with spot 10 on skin 8. Thermal heating of the skin surface forms a blister 12 containing interstitial fluid. Blister 12 is formed in skin 8 due to rapid heating caused by laser energy being rapidly absorbed in the meltable absorber substance 10 laying on the skin surface. The pulse energy of beam 3 and the number of pulses can be adjusted until a blister forms and then opens up to release the fluid inside. Once the parameters of these conditions are established, the process should be repeatable.

Figure 6:
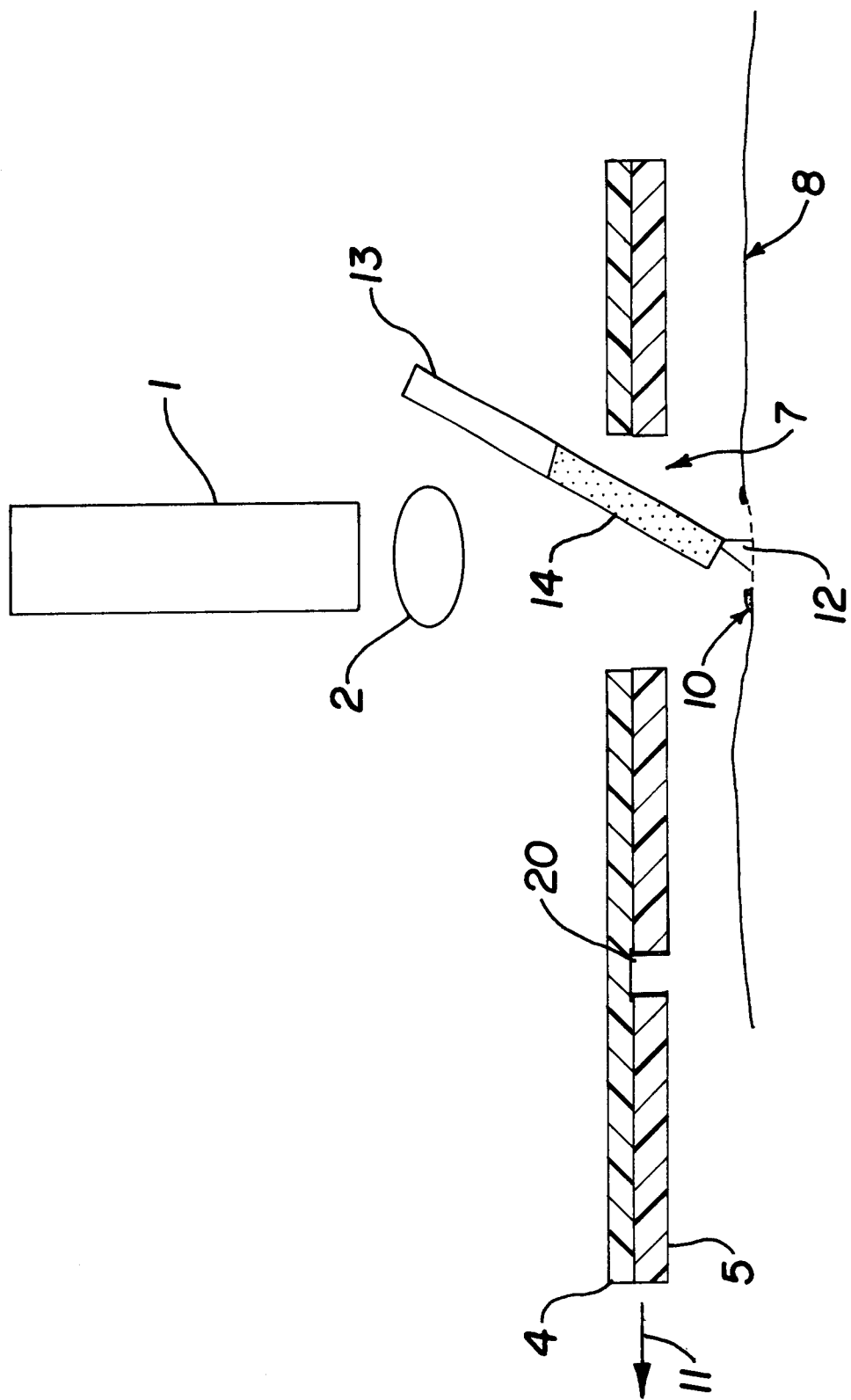
FIG. 6 illustrates a collection means for collecting the interstitial fluid from the ruptured blister of FIG. 5.

FIG. 6 illustrates one means of collection of the interstitial fluid from the ruptured blister. A collection means 13 is used to remove to interstitial fluid 14 from the surface of skin 8. Collections means 13 is illustrated in this Figure as a glass tube. The fluid is made available by rupturing the tiny blister in the skin. Surface tension draws the fluid into the tube where it is collected and may be transferred to a diagnostic device for measurements. The interstitial fluid volume collected would be expected to be fall within the range of about 25 nanoliters to about 25 microliters. It should be recognized to one skilled in the art that various means could be used to collect the interstitial fluid from the blister 12 on skin 8. This drawing, like the other drawings, is exaggerated to illustrate the invention. The blister that is formed in this process is very small.

Figure 7:
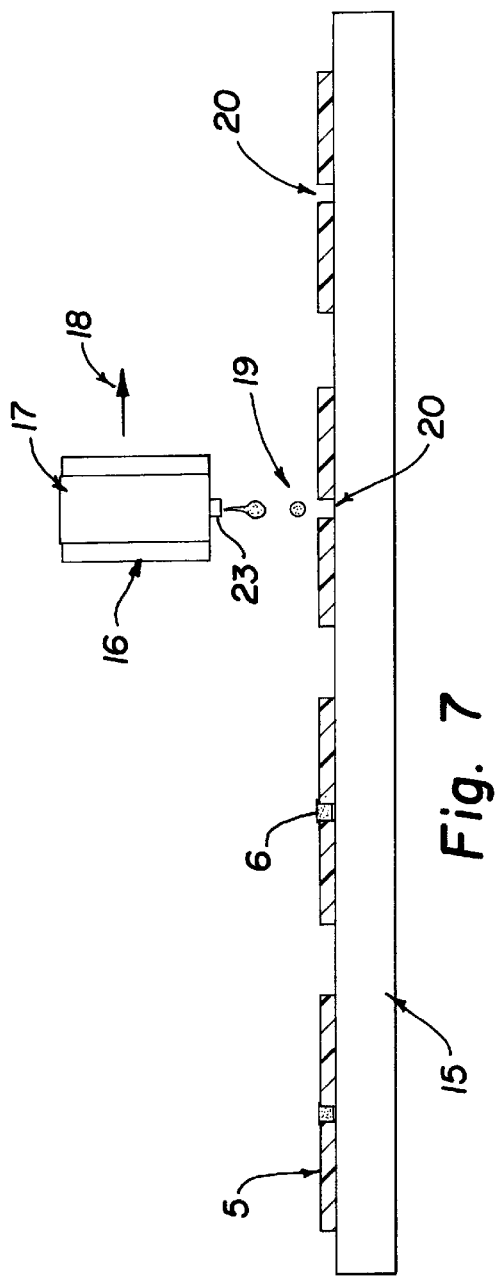
FIG. 7 is an elevational view of an automated means of placing the absorbing substance into holes in a sheet or strip of polymer film material containing previously formed openings.

FIG. 7 illustrates a means of making the laminated carrier film or substrate which contains the meltable absorber substance. More specifically, FIG. 7 illustrates a digitally controlled means of placing the meltable absorbing substance into holes 20 of a preferably polymer film or sheet substrate 5. Holes 20 in polymer film 5 have been previously made by excimer laser ablation or some other suitable process in a strip of material which, for example, might be wound on a reel. The film may have edge portions (not shown) which, in the manner of sprocket tracks on movie film, might hold the individual center portions together so they can be manipulated as a strip. It is also possible that the "film" 5 could be a strip of non-flexible material or a series of lengths of such material more in the nature of a batch process. Prototypes of the carrier strip have actually been made out of glass slides.

In FIG. 7 carrier film or strip 5 is supported on a support base 15. A digitally operated printhead 17 has an orifice 23 at its lower end in fluid communication with an internal reservoir, or is connected to a reservoir, containing the meltable absorber substance 6. Printhead 17 may be supplied with one or more heaters 16 for raising the temperature of the printhead so that the meltable materials would melt or have their viscosity reduced so as to have the appropriate fluid properties in the printhead for digitally jetting droplets from orifice 23 by means of modified ink jet technology. Strip 5 is shown positioned with an orifice 20 positioned directly under orifice 23. Printhead 17 is dispensing one or a plurality of droplets 19 of meltable absorbing substance 6 to fill holes 20 in film strip 5. This type of printhead could be similar to the ones described in U.S. Pat. Nos. 5,053,100, 5,498,444 and 5,772,106 which are hereby incorporated by reference.

The arrow 18 indicates relative movement between printhead 17 and base strip 5 in order to position orifice 23 over each successive opening 20. Although arrow 18 indicates movement of printhead 17, the strip 5 could be moved and positioned under a stationary printhead 17 as an alternative process. A mechanism (not shown) for moving either the strip 5 or the printhead 17 a specified distance or to a specified location by means of an X-Y stage is believed to be well known in the art and not actually a part of the present invention.

Figure 8:
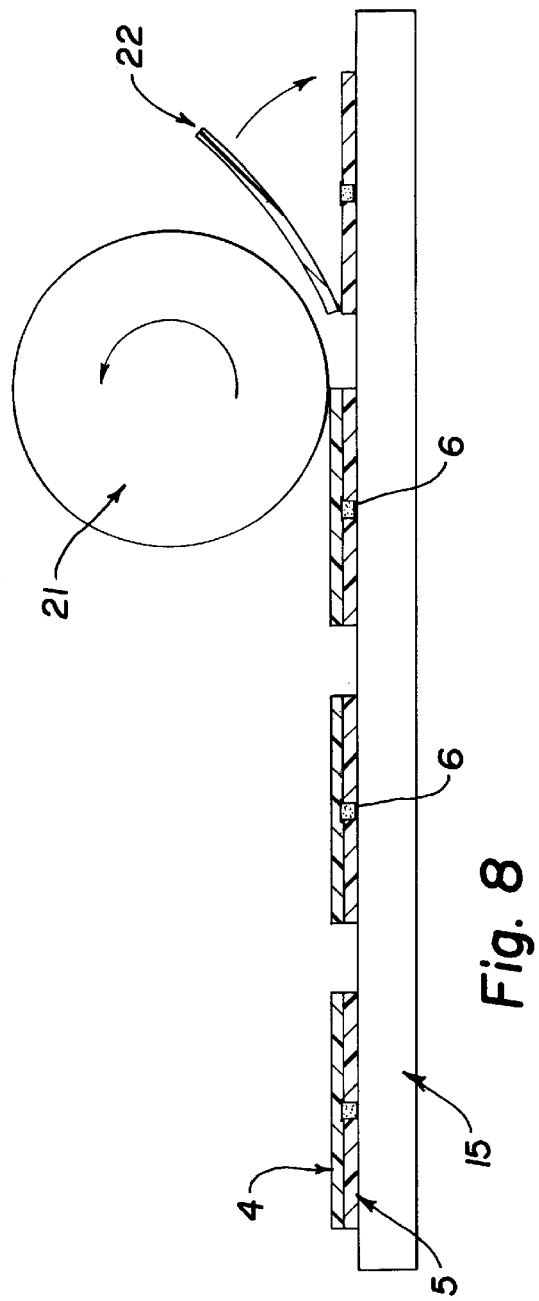
FIG. 8 is an elevational view the process of automatically attaching and laminating transparent film to the base film material of FIG. 7 containing the meltable absorber substance.

FIG. 8 illustrates a continuation of the process of FIG. 7 whereby the film strip layer 4 is laminated onto the top of base strip 5 to cover what will be the backside of the openings 20 now containing the meltable absorbing substance 6. This may be accomplished by a schematically illustrated laminated wheel 21 which presses the unbonded polymer film strip 22 onto the base strip 5 where it would be held in place by an adhesive. The adhesive could be preapplied to the film strip or applied in an inline process to either or both of the surfaces to be joined as shown in FIG. 8.

Figure 9:
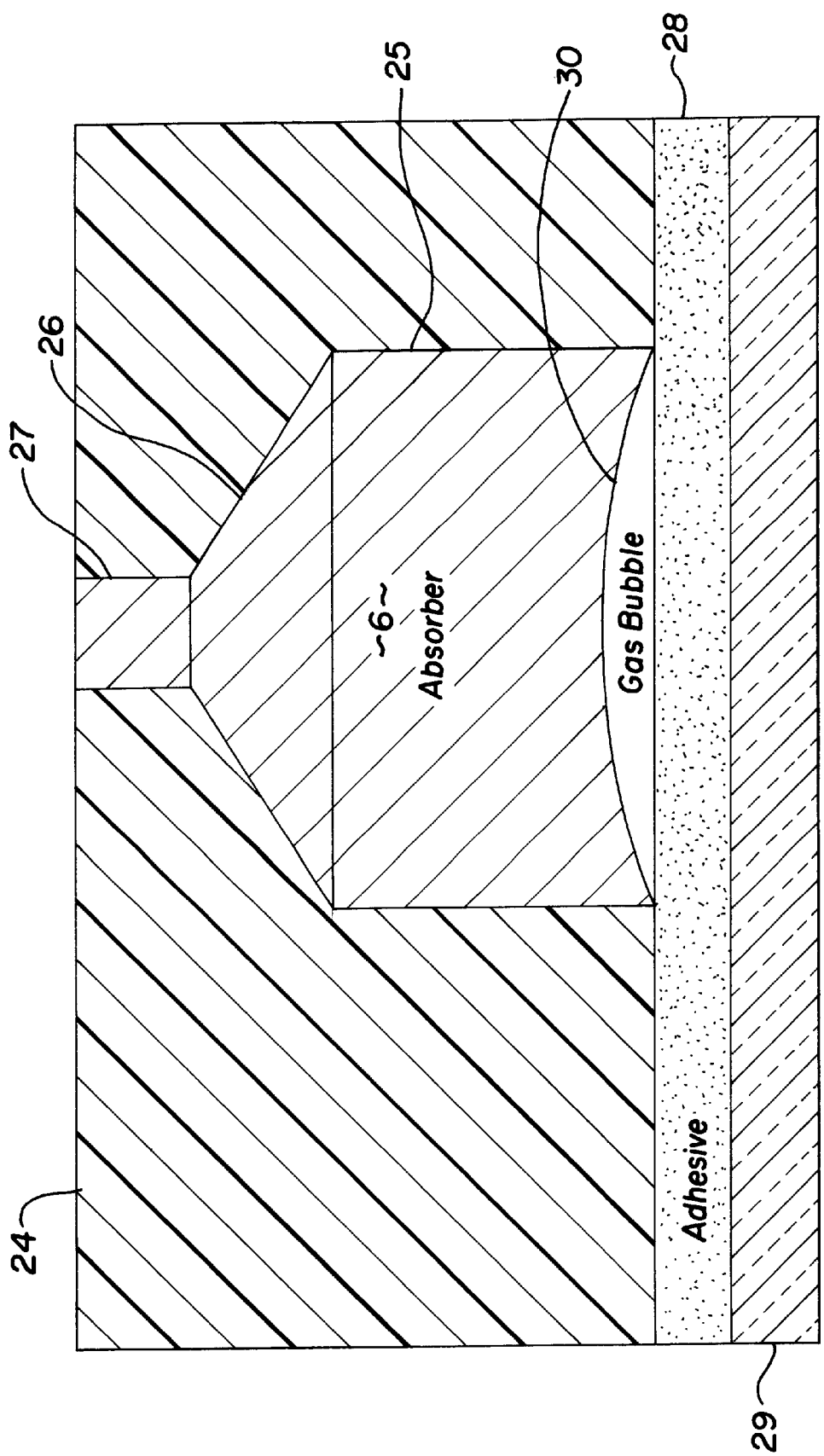
FIG. 9 is a cross sectional view of a prototype opening, containing the meltable absorber substance, which has a nozzle from which the substance is ejected and a gas bubble which enhances ejection.

In the best mode, FIG. 9 illustrates a current prototype of the invention. What is referred to as the film sheet 24 in FIG. 9 corresponds to the base sheet 5 in the previous Figures (the structure has been rotated 180°). The opening 25 corresponds to the opening containing meltable absorber substance 6 in the previous Figures and is shown as being filled with the substance 6. Opening 25 is a cylindrical shaped opening in film sheet 24. It has a conical portion 26 as a coincidence of producing opening 25 by means of a tiny drill. Opening 25 in film sheet 24 culminates in a nozzle 27 from which absorber substance will be projected. Film sheet 24 is made from Ultem® sheet which is adhesively joined by means of a UV curable optical adhesive 28 to a backing film sheet 29 corresponding to the film cover 4 in the previous Figures. In this particular embodiment, the cover material is actually a glass microscope slide. Absorber 6 is a high viscosity, paste-like dispersion of one or more colorants and/or pigments in a nonaqueous oleophilic base. Also shown is an optional gas bubble 30, in this case air. The presence of an air bubble seems to enhance the ejection of the droplet 9 from nozzle 27. It allows the absorber to expand on the side heated by the laser without pushing material out through the orifice. This means the gas in the gas bubble may become pressurized and ready to expand rapidly when the absorber becomes soft enough to flow through the orifice. The gas is capable of expanding rapidly, thus giving the ejected absorber substance a higher velocity than if a thermal expansion of the absorber substance were the only driving force. In this particular prototype the sheet 24 is about 0.015 inches thick with a nozzle which is approximately 0.002 inches in diameter. The main volume of the well which constitutes opening 25 and conical portion 26 is drilled with a 0.005 inches diameter drill to a depth that leaves about a 0.002 thickness for the nozzle to be drilled through. The diameter of the nozzle is approximately 50 micrometers and the diameter of the main portion of opening 25 is approximately 250 micrometers. The current absorber substance uses carbon black as a pigment.

We claim:

1. A method for releasing interstitial fluid from skin for collection or measurement, comprising:

providing a carrier film having at least one opening containing a meltable absorber substance selected to absorb energy from a laser beam;

placing the carrier film over skin with the absorber substance positioned facing the skin;

positioning a laser over the carrier film with the beam it produces directed upon the absorber substance; and melting the absorber substance by means of the laser beam and thereby ejecting the melted absorber substance from the at least one opening in the carrier film to the skin where it becomes a spot which can be used to absorb laser energy in a subsequent step to release interstitial fluid from the skin.

2. The method of claim 1 wherein the step of providing a carrier film comprises the step of providing clear polymer film on one side of said opening and the step of positioning the laser comprises the step of positioning the beam produced by the laser to pass through the clear film before it reaches the absorber substance.

3. The method of claim 2 wherein the step of providing a carrier strip with at least one opening comprises the step of providing said at least one opening with a nozzle and the step of melting the absorber substance and ejecting the melted absorber substance from the at least one opening is carried out by ejecting the absorber substance through the nozzle.

4. The method of claim 2 wherein the step of positioning the laser over the carrier film includes the step of focusing the beam it produces and the step of melting the absorber substance is performed with the focused laser beam.

5. The method of claim 1 wherein the step of providing the carrier film comprises the step of providing a carrier film having a plurality of said openings containing said meltable absorber substance and further includes the step of indexing the carrier film to position the laser with the beam it produces directed to a different opening containing said meltable absorber substance after melting and ejecting the absorber substance from an opening to which the laser beam the laser produces was previously directed.

6. The method of claim 5 wherein the step of providing a carrier film comprises the step of providing a clear polymer film on one side of said plurality of openings and the step of positioning the laser comprises the step of positioning the beam produced by the laser to pass through the clear polymer film before it reaches the absorber substance in any of the plurality of openings.

7. The method of claim 1 wherein the step of providing the carrier film comprises the step of providing a carrier strip having a plurality of said openings containing a meltable absorber substance arranged in a row and includes at least one aperture between a first one of said plurality of openings and a second one of said plurality of openings, further including the steps of:

operating the laser while directing the beam produced by the laser to the first one of said plurality of openings and thereby melting and ejecting the meltable absorber substance from the opening to form a spot of absorber substance on a person's skin; and placing the aperture between said first and second ones of said plurality of openings directly over the spot on a person's skin.

8. The method of claim 7 further comprising the step of operating the laser while directing the beam produced by the laser to the spot on the person's skin to form a small blister containing interstitial fluid.

9. The method of claim 8 further including the step of taking the interstitial fluid for analysis.

10. A method for releasing interstitial fluid from skin for collection or measurement, comprising:

providing a carrier film having at least one opening containing a meltable absorber substance selected to absorb energy from a laser beam, and at least one aperture in the carrier film adjacent said at least one opening;

placing the carrier film over skin with the absorber substance positioned facing the skin;

positioning a laser over the carrier film with the beam it produces directed upon the absorber substance;

melting the absorber substance by means of a laser beam and thereby ejecting the melted absorber substance from the at least one opening in the carrier film to the skin where it becomes a spot capable of absorbing laser energy;

indexing the carrier film relative to the skin so that the aperture is located between the spot of absorber substance on the skin and the beam produced by the laser; and operating the laser, while directing the beam produced by the laser to the spot of absorber substance on the skin, to thereby create a tiny blister containing interstitial fluid on the skin in the area where the spot was formed.

11. The method of claim 10 further including the step of taking the interstitial fluid from the blister for analysis.

12. The method of claim 10 wherein the step of providing a carrier film having at least one opening comprises the step of providing clear polymer film on one side of said opening and the step of positioning the laser comprises the step of positioning the beam produced by the laser to pass through the clear film before it reaches the absorber substance.

13. The method of claim 10 wherein the step of providing a carrier film comprises the step of providing a carrier film having a plurality of said openings containing said meltable absorber substance and the step of positioning the laser over the carrier film comprises the step of positioning the beam produced by the laser to pass through the clear polymer film before it reaches the absorber substance in any given one of the plurality of openings.

* * * * *

UNITED STATES PATENT AND TRADEMARK OFFICE
CERTIFICATE OF CORRECTION

PATENT NO. : 6,334,851 B1
DATED : January 1, 2002
INVENTOR(S) : Donald J. Hayes et al.

It is certified that error appears in the above-identified patent and that said Letters Patent is hereby corrected as shown below:

Column 1,
Line 8, insert -- 35 U.S.C.-- after "under"

Column 3,
Line 55, replace "tat" with -- at --.

Column 4,
Line 37, insert -- in the direction of arrow 11 -- after "indexed".

Column 6,
Line 58, replace "strip" with -- film --.

Signed and Sealed this

Twenty-seventh Day of August, 2002

Attest:

JAMES E. ROGAN
Attesting Officer　　Director of the United States Patent and Trademark Office